(12) United States Patent
Nagy (10) Patent No.: US 11,051,639 B1
(45) Date of Patent: Jul. 6, 2021

(54) VARIABLE PRESSURE BLANKET

(71) Applicant: William Nagy, Chandler, AZ (US)

(72) Inventor: William Nagy, Chandler, AZ (US)

(*) Notice: Subject to any disclaimer, the term of this patent is extended or adjusted under 35 U.S.C. 154(b) by 0 days.

(21) Appl. No.: 16/783,853

(22) Filed: Feb. 6, 2020

(51) Int. Cl.
*A47G 9/02* (2006.01)
*A47G 9/00* (2006.01)

(52) U.S. Cl.
CPC ............ *A47G 9/023* (2013.01); *A47G 9/007* (2013.01); *A47G 9/0223* (2013.01)

(58) Field of Classification Search
CPC ...... A47G 9/023; A47G 9/0223; A47G 9/007; A47G 9/02; A47G 9/0284; A47G 9/08; A47G 9/086; B68G 2001/005; B68G 7/06
USPC .......................................................... 5/502
See application file for complete search history.

(56) References Cited

U.S. PATENT DOCUMENTS

| | | | | | |
|---|---|---|---|---|---|
| 4,839,934 | A * | 6/1989 | Rojas | ............ | A47G 9/0207 5/485 |
| 5,199,121 | A * | 4/1993 | Payne | ............ | A47G 9/0207 5/413 R |
| 5,706,535 | A * | 1/1998 | Takashima | ............ | A47G 9/007 5/485 |
| 6,094,759 | A * | 8/2000 | Thompson | ............ | A47G 9/0223 5/420 |
| 7,814,589 | B2 * | 10/2010 | Loh | ............ | A47G 9/0207 5/502 |
| 7,870,623 | B2 * | 1/2011 | Judd | ............ | A61H 7/001 5/502 |
| 8,707,480 | B2 * | 4/2014 | Graddy | ............ | A47G 9/023 5/486 |
| 2005/0273930 | A1 * | 12/2005 | Phillipps | ............ | A47G 9/023 5/486 |
| 2006/0016005 | A1 * | 1/2006 | Roda | ............ | A41B 13/06 5/482 |
| 2006/0031987 | A1 * | 2/2006 | Stanfield | ............ | A47G 9/0207 5/486 |
| 2007/0101496 | A1 * | 5/2007 | Ho | ............ | A47G 9/02 5/497 |
| 2007/0157383 | A1 * | 7/2007 | Burns | ............ | A47G 9/0207 5/486 |
| 2007/0169264 | A1 * | 7/2007 | Spicer | ............ | A47G 9/0207 5/486 |

(Continued)

FOREIGN PATENT DOCUMENTS

WO     WO2014166557 A1 * 10/2014 ............. A47G 9/007

*Primary Examiner* — Nicholas F Polito
*Assistant Examiner* — Luke Hall
(74) *Attorney, Agent, or Firm* — Goldstein Law Offices, P.C.

(57) ABSTRACT

A variable pressure blanket is disclosed. The variable pressure blanket includes a casing having a top fabric stitched to a bottom fabric to form a plurality of pockets having an interior volume. Discrete regions are arranged laterally across the casing to form distinct regions within the blanket. Each of the discrete regions have some of the pockets therein. Fill particles are disposed within the interior volumes of each of the pockets to generate a downward pressure. The pockets within one of the discrete regions have more fill particles than the pockets within the other discrete regions so that the one discrete region generates a greater downward pressure than the other discrete regions. The fill particles are non-insulative, while the top fabric and the bottom fabric may comprise an insulative material.

20 Claims, 6 Drawing Sheets

(56) References Cited

U.S. PATENT DOCUMENTS

| | | | | |
|---|---|---|---|---|
| 2007/0277315 | A1* | 12/2007 | Loh | A47G 9/0207 5/502 |
| 2008/0313809 | A1* | 12/2008 | Inman, II | A47G 9/0207 5/486 |
| 2011/0047698 | A1* | 3/2011 | Parker | A47G 9/0207 5/502 |
| 2013/0191991 | A1* | 8/2013 | Graddy | A47G 9/023 5/502 |
| 2014/0373277 | A1* | 12/2014 | Fan | A47G 9/0223 5/502 |
| 2015/0013068 | A1* | 1/2015 | Werthaiser | A47G 9/0207 5/502 |
| 2017/0340131 | A1* | 11/2017 | Schmidt | A47G 9/10 |
| 2018/0035832 | A1* | 2/2018 | Ureten | A61M 21/02 |
| 2018/0317674 | A1* | 11/2018 | Richard | A47G 9/0223 |
| 2019/0021525 | A1* | 1/2019 | Hamm | B32B 3/06 |

* cited by examiner

VARIABLE PRESSURE BLANKET

TECHNICAL FIELD

The present disclosure relates generally to blankets. More particularly, the present disclosure relates to a variable pressure blanket including at least two regions of varying pressure formed by non-insulative fill particles.

BACKGROUND

Blankets having added weight are very popular for a number of reasons. For one, the pressure exerted onto an individual by the blanket produces a calming effect in the individual. Indeed, weighted blankets are known to use principles of Deep Touch Pressure (DTP) or Deep Pressure Stimulation (DPS) to improve relaxation. They are used largely by adults to treat anxiety, insomnia, and other common problems. Moreover, weighted blankets are used to treat children with disorders like Autistic Spectrum Disorder, Attention-Deficit/Hyperactivity Disorder (ADHD), and Pervasive Developmental Disorder Not Otherwise Specified (PDD-NOS).

Weighted blankets include a weighted material distributed evenly across the blanket such that the blanket applies equal pressure to all parts of the body. It is common that these weighted blankets are shared by partners on their bed. However, it is often the case that the blanket pressure preferred by one partner is not the preferred blanket pressure of the other partner. As such, known weighted blankets are disadvantageous because they do not provide varying blanket pressure vertically across the blanket to accommodate different desired blanket pressure by individuals sharing the blanket.

Moreover, it is common that individuals want a different blanket pressure over different regions of their body. As such, known weighted blankets are disadvantageous because they do not provide varying blanket pressure horizontally across the blanket to accommodate different desired blanket pressure to different regions on the individual's body.

Accordingly, there is a need for a variable pressure blanket that provides different pressure distribution vertically across two or more regions of the blanket or horizontally across two or more regions of the blanket.

While these units may be suitable for the particular purpose employed, or for general use, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a variable pressure blanket. Accordingly, the present disclosure provides a variable pressure blanket having regions that generate different pressure across the blanket.

An aspect of an example embodiment in the present disclosure is to provide a variable pressure blanket having regions that generate different pressures across a width of the blanket. Accordingly, the present disclosure provides a variable pressure blanket having at least two regions longitudinally disposed across the blanket that generate different pressure with respect to one another.

An aspect of an example embodiment in the present disclosure is to provide a variable pressure blanket having regions that generate different pressure across a length of the blanket. Accordingly, the present disclosure provides a variable pressure blanket having two or more regions disposed widthwise across the blanket that generate different pressure with respect to one another.

An aspect of an example embodiment in the present disclosure is to provide a variable pressure blanket having a pressure gradient. Accordingly, the present disclosure provides a variable pressure blanket having a pressure gradient extending laterally across the blanket that either decreases or increases in pressure vertically or horizontally.

An aspect of an example embodiment in the present disclosure is to provide a variable pressure blanket that generates pressure with non-insulative materials. Accordingly, the present disclosure provides a variable pressure blanket having non-insulative fill particles that generate a downward pressure.

An aspect of an example embodiment in the present disclosure is to provide a variable pressure blanket that generates pressure while maintaining a uniform casing, fabric, and/or batting thickness throughout. Accordingly, the present disclosure provides a variable pressure blanket having a casing including a top fabric and a bottom fabric that include a uniform thickness and/or weight.

An aspect of an example embodiment in the present disclosure is to provide a method of making a variable pressure blanket that includes at least two regions that each generate different pressures. Accordingly, the present disclosure provides a method of making a variable pressure blanket comprising at least two regions that generate different pressure by distributing fill particles across a bottom fabric, dividing the fill particles into at least two discrete regions across the bottom fabric, wherein one of the discrete regions includes more fill particles than the other of the discrete regions, and stitching a top fabric to the bottom fabric to secure the fill particles within pockets within the blanket.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION

Figure 1:
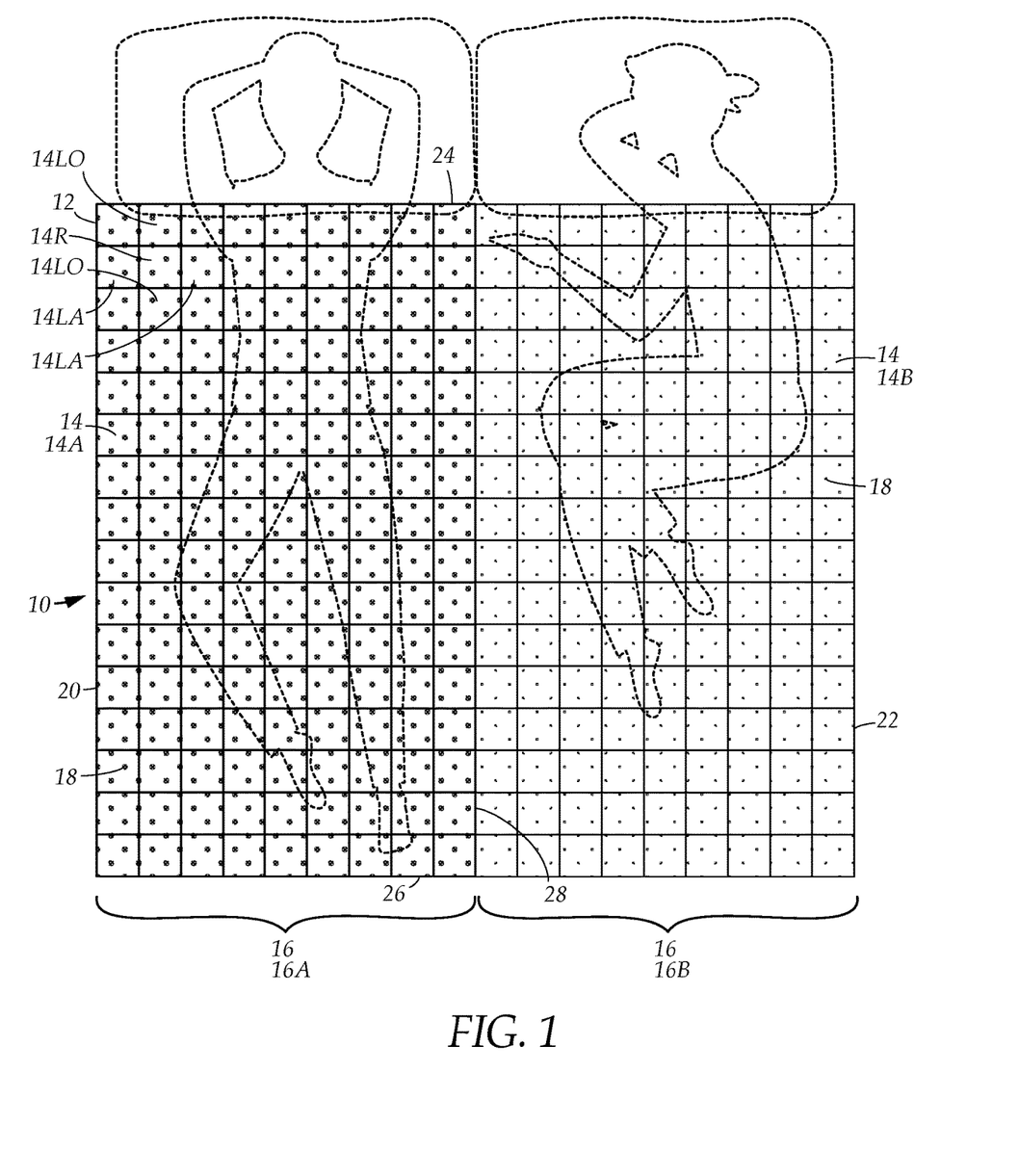
FIG. 1 is plan view of the variable pressure blanket in use, illustrating two vertically extending discrete regions disposed longitudinally across the variable pressure blanket, each generating a different pressure according to one embodiment of the present disclosure.

FIG. 1 illustrates a variable pressure blanket 10 comprising a casing 12 stitched to form a plurality of pockets 14 and at least two discrete regions 16 arranged laterally across the casing 12. The plurality of pockets 14 include laterally positioned directly adjacent pockets 14LA and longitudinally positioned directly adjacent pockets 14LO with respect to a reference pocket 14R. Note, the reference pocket 14R may be any one of the plurality of pockets 14. The plurality of pockets 14 include an interior volume 17 (see FIG. 6) containing solid fill particles 18, such that all of the directly adjacent pockets including the laterally positioned directly adjacent pockets and the longitudinally positioned directly adjacent pockets include solid fill particles 18. The fill particles 18 include a mass that generates a downward pressure on the casing 12 so as to exert a downward pressure on an individual or individuals using the blanket 10. Each of the discrete regions 16 comprises some of the pockets 14 therewithin. In some embodiments, the discrete regions 16 include substantially the same number of pockets 14 as one another. In other embodiments, the discrete regions 16 comprise substantially equal dimensions as one another. In alternative embodiments, the discrete regions 16 comprise different dimensions as one another.

The pockets 14 within one discrete region 16 contain more fill particles 18 than the pockets 14 of a separate discrete region 16, such that the one discrete region 16 generates a different downward pressure than the separate discrete region 16. In this way, the blanket 10 is capable of exerting a downward pressure in one region of the blanket 10 and a different downward pressure in another region of the blanket 10. Of course, the term "more" does not limit the fill particles 18 to the quantity, amount, or number of fill particles 18 within the pockets 14, but rather also includes a mass of the fill particles 18.

For example, in embodiments, the variable pressure blanket comprises a first discrete region 16A and a second discrete region 16B arranged laterally across the blanket 10. The first discrete region 16A comprises pockets 14A and the second discrete region 16B comprises pockets 14B. The first discrete region 16A has more fill particles 18 distributed amongst its pockets 14A than the second discrete region 16B has distributed amongst its pockets 14B, thereby generating a greater overall downward pressure than the second discrete region 16B. In another embodiment, the first discrete region 16A has a larger overall mass of fill particles 18 distributed amongst its pockets 14A than the second discrete region 16B has distributed amongst its pockets 14B. The larger overall mass of fill particles 18 in the first discrete region 16A as compared to the second discrete region 16B is independent of the quantity of fill particles 18 in that the first discrete region 16A can comprise a larger overall mass of fill particles 18 distributed amongst its pockets 14A than the second discrete region 16B has distributed amongst its pockets 14B, while still having a smaller quantity of fill particles 18 distributed amongst its pockets 14A than the second discrete region 16B has distributed amongst is pockets 14B.

The casing 12 includes a first longitudinal edge 20 opposing a second longitudinal edge 22, a first lateral edge 24 opposing a second lateral edge 26, and a center 28 extending from the first lateral edge 24 to the second lateral edge 26. The discrete regions 16 extend vertically across a length of the casing 12 from the first lateral edge 24 to the second lateral edge 26. In one embodiment, the casing 12 comprises two discrete regions 16A, 16B including equal dimensions. The first discrete region 16A extends from the first lateral edge 24 to the second lateral edge 26 and from the first longitudinal edge 20 to the center 28, while the second discrete region 16B extends from the first lateral edge 24 to the second lateral edge 26 and from the second longitudinal edge 22 to the center 28.

Figure 5:
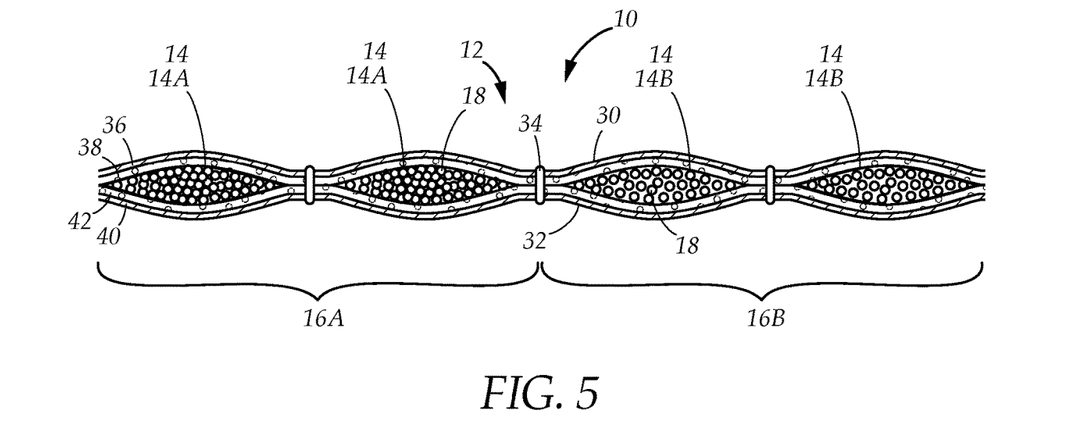
FIG. 5 is a cross-sectional view of the variable pressure blanket, illustrating the fill particles of the pockets within one discrete region and the fill particles of the pockets within a separate discrete region to demonstrate the distribution of fill particles across the discrete regions of the blanket according to one embodiment of the present disclosure.
Figure 6:
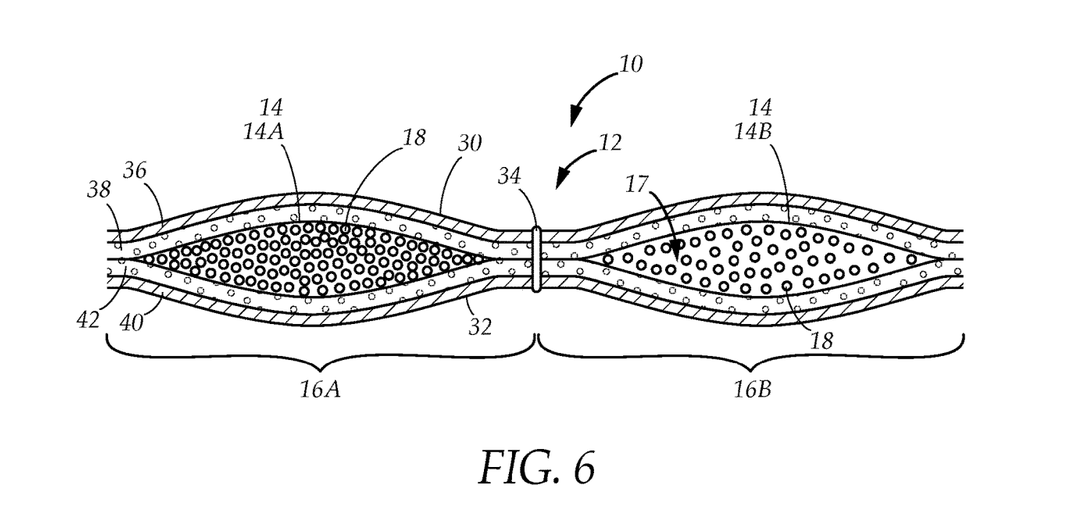
FIG. 6 is a cross-sectional view of the variable pressure blanket, illustrating a close-up view of the fill particles of a pocket within one discrete region and the fill particles of another pocket within a separate discrete region to demonstrate the distribution of fill particles across the discrete regions of the blanket according to one embodiment of the present disclosure.

FIGS. 5 and 6 show an interior of the casing 12 and pockets 14 of the variable pressure blanket 10. The casing 12 includes a top fabric 30 and a bottom fabric 32 connected together via stitches 34 to form the pockets 14. The stitches 34 separate and define all directly adjacent pockets, e.g., the laterally positioned directly adjacent pockets 14LA, the longitudinally positioned directly adjacent pockets 14LO, and the reference pockets 14R (see FIG. 1). The top fabric 30 and the bottom fabric 32 each comprises a uniform thickness and weight. In one embodiment, the top fabric 30 and the bottom fabric 32 include the same thickness and weight. The top fabric 30 and the bottom fabric 32 includes material having insulative heating and/or cooling properties. The top fabric 30 comprises an outer layer 36 and an inner layer 38. The bottom fabric 32 also comprises an outer layer 40 and an inner layer 42. In embodiments, the inner layers 38, 42 comprise batting.

The fill particles 18 comprise particles including non-insulative heating and/or cooling properties. The fill particles 18 form no part of the top fabric 30 and bottom fabric 32 of the casing 12. In some embodiments, the fill particles 18 include a uniform mass and/or size. In other embodiments, the fill particles 18 comprise a non-uniform mass and/or size. The fill particles 18 comprise glass beads having a predetermined mass and/or size.

The pockets 14 comprise substantially equal interior volumes 17. The fill particles 18 are distributed amongst the interior volumes 17 of the pockets 14 such that all the pockets 14 within a discrete region 16 have substantially equal densities of fill particles 18 to generate substantially the same downward pressure as one another. When the pockets 14 within a discrete region 16 generate the same downward pressure as one another, the pockets 14 generate a substantially uniform downward pressure across the discrete region 16.

For example, in embodiments, all of the pockets 14A within the first discrete region 16A include approximately the same quantity of fill particles 18 as one another, while the pockets 14B of the second discrete region 16B include approximately the same quantity of fill particles 18 as one another. In this embodiment, the fill particles 18 include a uniform mass. In another embodiment, the pockets 14A within the first discrete region 16A include a different quantity of fill particles 18 as one another but include the same density as one another due to a substantially equal mass of fill particles 18 within the individual pockets 14. In this embodiment, the fill particles 18 used to fill the pockets 14 may include a non-uniform mass and size.

Figure 2:
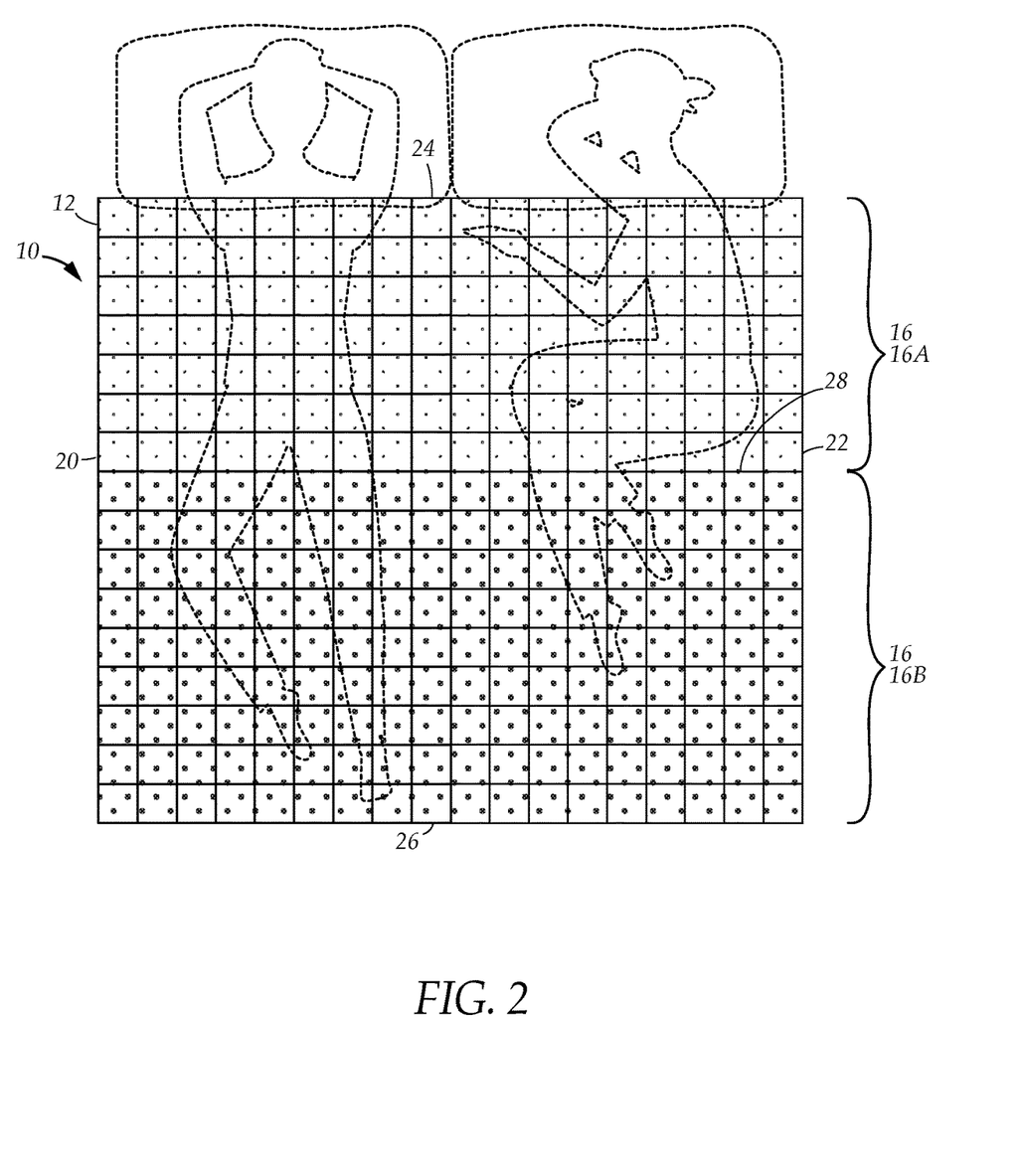
FIG. 2 is a plan view of the variable pressure blanket in use, illustrating two horizontally extending discrete regions disposed widthwise across the variable pressure blanket, each generating a different pressure according to one embodiment of the present disclosure.

FIG. 2 shows another embodiment of the variable pressure blanket 10. In some embodiments, the casing 12 includes a first longitudinal edge 20 opposing a second longitudinal edge 22, a first lateral edge 24 opposing a second lateral edge 26, and a center 28 extending from the first longitudinal edge 20 to the second longitudinal edge 22. The discrete regions 16 extend horizontally across a width of the casing 12 from the first longitudinal edge 20 to the second longitudinal edge 22. In one embodiment, the casing 12 comprises a first discrete region 16A and a second discrete region 16B including equal dimensions. The first discrete region 16A extends from the first longitudinal edge 20 to the second longitudinal edge 22 and from the first lateral edge 24 to the center 28, while the second discrete region 16B extends from the first longitudinal edge 20 to the second longitudinal edge 22 and from the second lateral edge 26 to the center 28.

Figure 3:
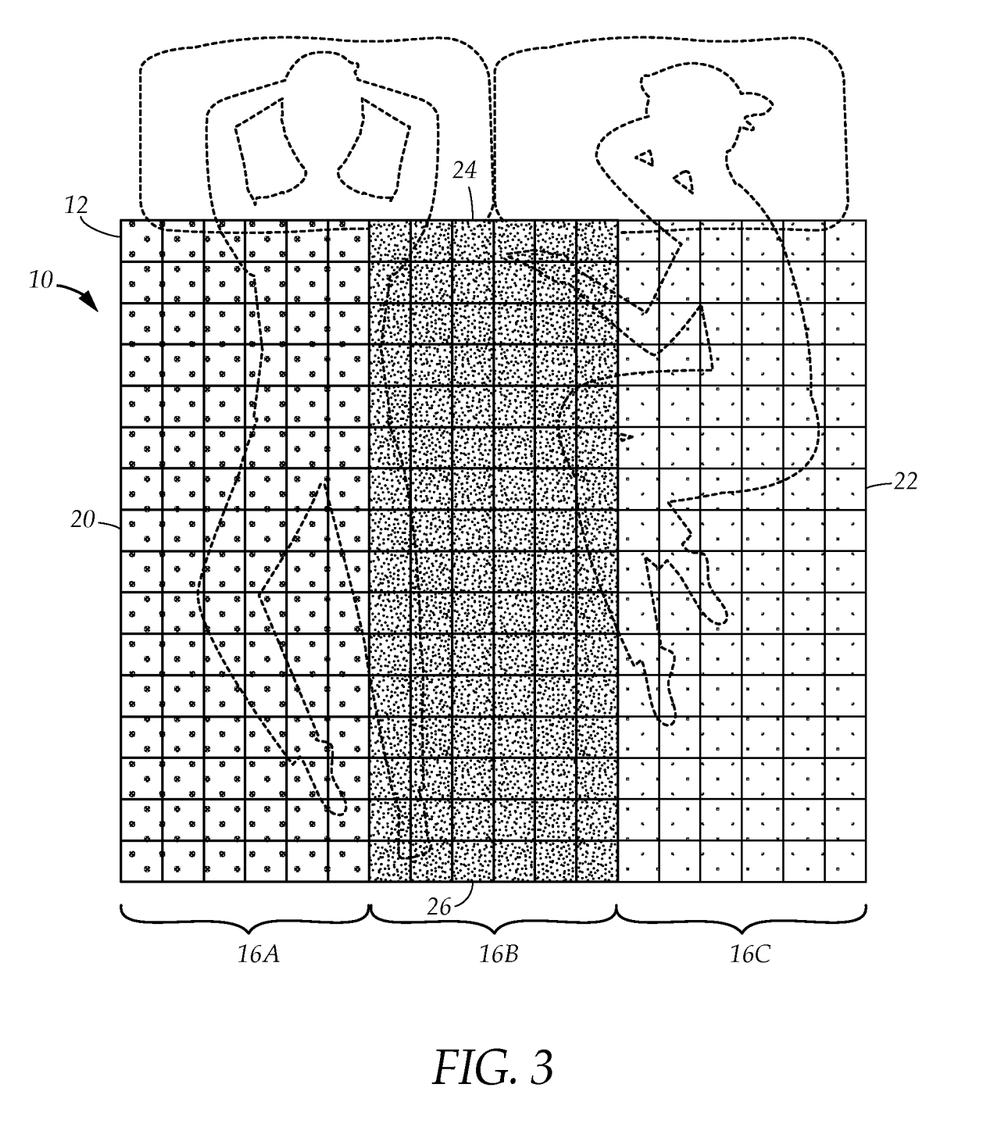
FIG. 3 is a plan view of the variable pressure blanket in use, illustrating three vertically extending discrete regions disposed longitudinally across the variable pressure blanket, each generating a different pressure according to one embodiment of the present disclosure.

FIG. 3 shows an alternative embodiment of the variable pressure blanket 10. The casing 12 includes a first longitudinal edge 20 opposing a second longitudinal edge 22, a first lateral edge 24 opposing a second lateral edge 26 and extending from the first lateral edge 24 to the second lateral edge 26. The casing 12 comprises three discrete regions 16A, 16B, 16C that are divided in equal dimensions across the blanket 10. The discrete regions 16A, 16B, 16C extend vertically across the length of the casing 12 from the first lateral edge 24 to the second lateral edge 26.

Figure 4:
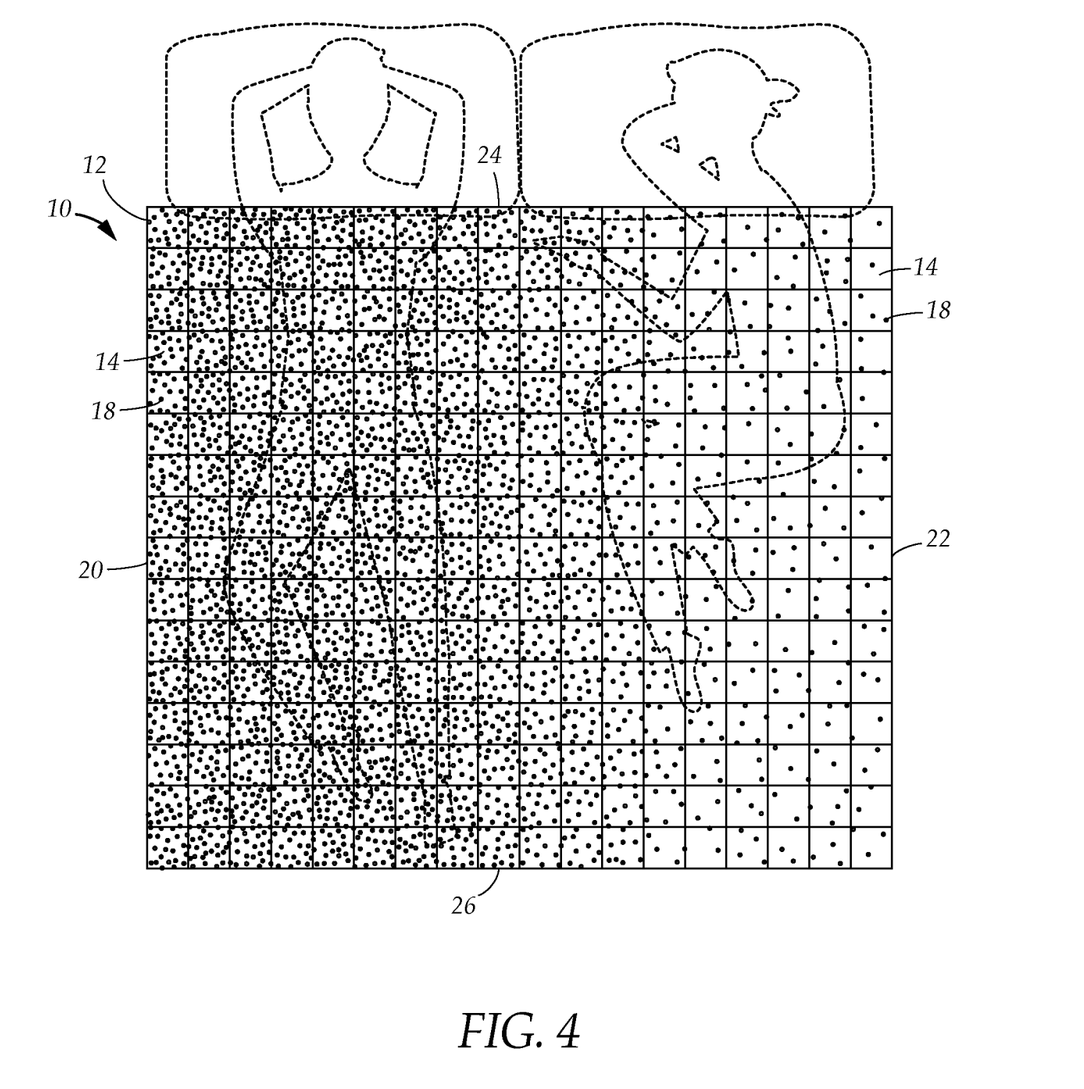
FIG. 4 is a plan view of the variable pressure blanket in use, illustrating a pressure distribution gradient extending laterally across the blanket according to one embodiment of the present disclosure.

FIG. 4 shows yet another embodiment of the variable pressure blanket 10. In embodiments, the fill particles 18 are divided amongst the pockets 14 to provide a pressure gradient laterally across the casing 12. In these embodiments, the pockets 14 decrease or increase in fill particle quantity and/or fill particle mass laterally across the casing 12. In some embodiments, the pressure gradient decreases in pressure from the first longitudinal edge 20 to the second longitudinal edge 22 while remaining constant from the first lateral edge 24 to the second lateral edge 26. In other embodiments, the pressure gradient decreases in pressure from the first lateral edge 24 to the second lateral edge 26 while remaining constant from the first longitudinal edge 20 to the second longitudinal edge 22. In one embodiment, the pressure gradient is formed by a decrease in the density of the fill particles 18 from the first longitudinal edge 20 to the second longitudinal edge 22 or vice versa. In another embodiment, the pressure gradient is formed by a decrease in the quantity of fill particles from the first longitudinal edge 20 to the second longitudinal edge 22 or vice versa.

Figure 7:
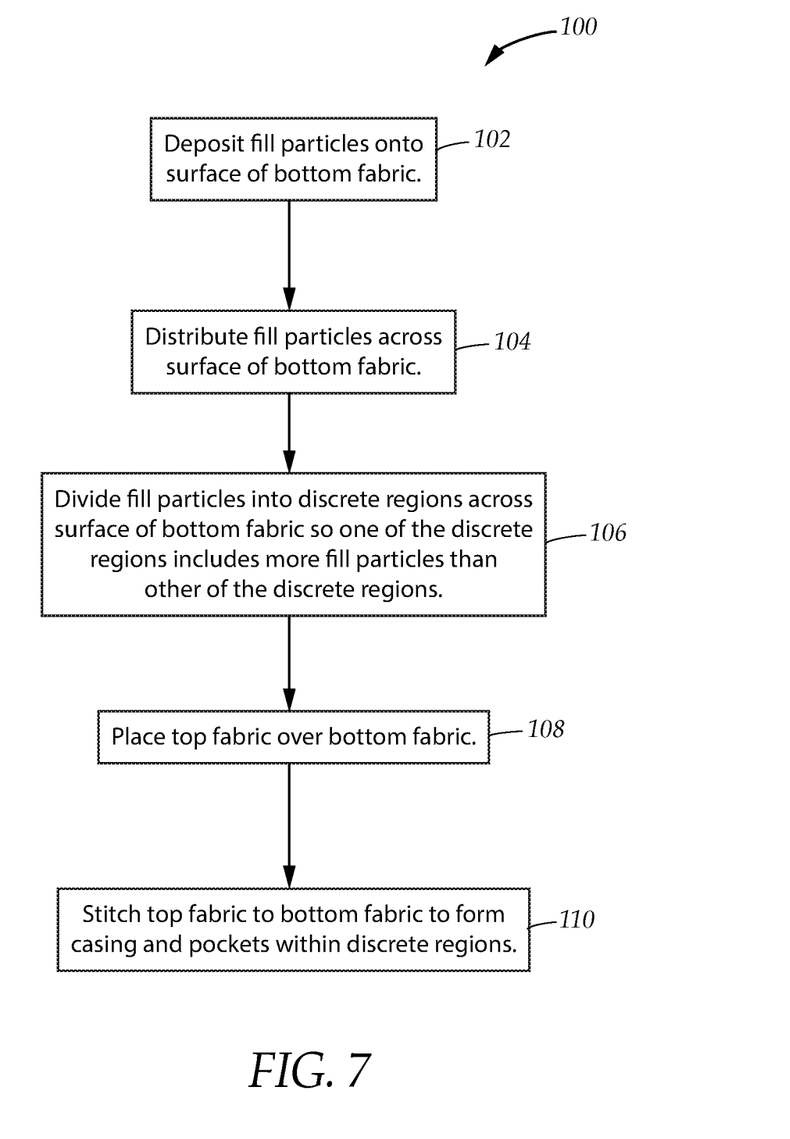
FIG. 7 is a flow chart of a method of making the variable pressure blanket, illustrating one manner in which the variable pressure blanket is made according to one embodiment of the present disclosure.

FIG. 7 shows a flow chart of a method 100 of making the variable pressure blanket. The method 100 includes depositing the fill particles onto a surface of the bottom fabric 102, distributing the fill particles across the surface of the bottom fabric 104, dividing the fill particles into the at least two discrete regions laterally across the surface of the bottom fabric to form discrete regions, wherein one of the discrete regions includes more fill particles than the other of the discrete regions 106, placing a top fabric over the bottom fabric 108, and stitching the top fabric to the bottom fabric to form the casing and the pockets within each discrete region 110 which would hold the fill particles therein. The formed pockets within a discrete region each have substantially equal interior volumes and substantially equal densities of fill particles as one another.

In embodiments, the method 100 includes depositing a first quantity of fill particles on the surface of the bottom fabric corresponding to one region of the at least two discrete regions and depositing a next quantity of fill particles on the surface of the bottom fabric corresponding to the other of the discrete regions. The first quantity of fill particles corresponds to a predetermined pressure and the next quantity of fill particles corresponds to a different predetermined pressure, such that the one discrete region generates a different pressure than the other discrete regions.

In some embodiments, the method 100 includes distributing a first quantity of fill particles across one region of the at least two discrete regions and then distributing a next quantity of fill particles across the other of the discrete regions, wherein the first quantity is larger than the next quantity such that the one discrete region includes more fill particles than the other discrete regions.

In other embodiments, the method 100 includes distributing the fill particles across the surface of the bottom fabric to all edges of the bottom fabric such that they are evenly dispersed across the entire surface of the bottom fabric. In certain embodiments, the method 100 includes aligning the edges of the top fabric with the edges of the bottom fabric so that the top fabric and bottom fabric are coterminous when stitched. In alternative embodiments, the method 100 includes stitching a seam along the boundary of the at least two discrete regions to separate them via a seam.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a variable pressure blanket. The disclosure is illustrated by example in the drawing figures, and throughout the written description. It should be understood that numerous variations are possible, while adhering to the inventive concept. Such variations are contemplated as being a part of the present disclosure.

What is claimed is:

1. A variable pressure blanket, comprising:
a unitary casing including a first longitudinal edge, a second longitudinal edge opposite the first longitudinal edge, a first lateral edge, a second lateral edge opposite the first lateral edge, a top fabric extending continuously between the first longitudinal edge, the second longitudinal edge, the first lateral edge, and the second lateral edge, the casing also including a bottom fabric extending continuously between the first longitudinal edge, the second longitudinal edge, the first lateral edge, and the second lateral edge, the top fabric stitched directly to a bottom fabric to form a plurality of pockets including laterally positioned directly adjacent pockets and longitudinally positioned directly adjacent pockets with respect to any one of the plurality of pockets, all of the directly adjacent pockets separated by stitching, the stitching defining all of the directly adjacent pockets, the pockets having interior volumes;
at least two discrete regions arranged laterally between the first longitudinal edge and the second longitudinal edge, each of the discrete regions including some of the pockets; and
rigid fill particles disposed within the interior volumes of each of the plurality of pockets such that all of the directly adjacent pockets including the laterally positioned directly adjacent pockets and the longitudinally positioned directly adjacent pockets within each discrete region include rigid fill particles of substantially uniform mass and size, the fill particles generating a downward pressure from the bottom fabric, each of the pockets in one of the at least two discrete regions including more fill particles than the pockets in the other of the at least two discrete regions so that the one of the at least two discrete regions generates a greater downward pressure from the bottom fabric than the other of the at least two discrete regions.

2. The variable pressure blanket of claim 1, wherein:
the top fabric
and the bottom fabric span all of the pockets and are stitched together to form a permanent connection;
all of the pockets within each discrete region comprise:
substantially equal interior volumes; and
substantially equal densities of fill particles to provide substantially the same downward pressure as one another to provide a substantially uniform downward pressure across each discrete region; and
each of the plurality of pockets includes a lateral side and a longitudinal side, each pocket sharing a lateral side and a longitudinal side with a directly adjacent pocket.

3. The variable pressure blanket of claim 2, wherein:
the pockets within each discrete region all comprise substantially the same quantity of fill particles as one another; and
the lateral side and the longitudinal side of each of the plurality of pockets includes a length, the length of the lateral side of each of the plurality of pockets defining the length of the lateral side of a laterally positioned directly adjacent pocket, the length of a longitudinal side of each of the plurality of pockets defining the length of the longitudinal side of a longitudinally positioned directly adjacent pocket.

4. The variable pressure blanket of claim 3, wherein:
the top fabric comprises a uniform thickness and weight; and
the bottom fabric comprises a uniform thickness and weight.

5. The variable pressure blanket of claim 4, wherein:
the top fabric and the bottom fabric comprise insulative material; and
the fill particles are non-insulative.

6. The variable pressure blanket of claim 5, wherein:
the casing includes a center; and
the discrete regions extend vertically across the casing from the first lateral edge to the second lateral edge.

7. The variable pressure blanket of claim 6, wherein the casing comprises two discrete regions including equal dimensions, a first discrete region extending from the first lateral edge to the second lateral edge and from the first longitudinal edge to the center of the casing; and a second discrete region extending from the first lateral edge to the second lateral edge and from the second longitudinal edge to the center.

8. The variable pressure blanket of claim 6, wherein the casing comprises three discrete regions divided in equal dimensions across the casing.

9. The variable pressure blanket of claim 5, wherein:
the casing includes a center; and
the discrete regions extend horizontally across the casing from the first longitudinal edge to the second longitudinal edge.

10. The variable pressure blanket of claim 9, wherein the casing comprises two discrete regions including equal dimensions, a first discrete region extending from the first longitudinal edge to the second longitudinal edge and from the first lateral edge to the center and a second discrete region extending from the first longitudinal edge to the second longitudinal edge and from the second lateral edge to the center.

11. The variable pressure blanket of claim 5, wherein:
the top fabric comprises an outer layer and an inner layer; and
the bottom fabric comprises an outer layer and an inner layer.

12. The variable pressure blanket of claim 11, wherein:
the inner layer of the top fabric comprises batting; and
the inner layer of the bottom fabric comprises batting.

13. A variable pressure blanket, comprising:
a casing including a top fabric and a bottom fabric, the top fabric stitched directly to the bottom fabric to form a plurality of pockets including substantially equal interior volumes, the plurality of pockets including laterally positioned directly adjacent pockets and longitudinally positioned directly adjacent pockets with respect to any one of the plurality of pockets, all of the directly adjacent pockets separated by stitching, the stitching defining all of the directly adjacent pockets,
rigid fill particles disposed within the interior volume of each of the plurality of pockets such that directly adjacent pockets including the laterally positioned directly adjacent pockets and the longitudinally positioned directly adjacent pockets include rigid fill particles of substantially uniform mass and size, the fill particles exerting a downward pressure;
wherein the fill particles are distributed amongst the pockets to provide a pressure gradient laterally across the casing.

14. The variable pressure blanket of claim 13, wherein:
the rigid fill particles of directly adjacent pockets including the laterally positioned directly adjacent pockets and the longitudinally positioned directly adjacent pockets include substantially equal densities;
the casing includes a first longitudinal edge opposing a second longitudinal edge and a first lateral edge opposing a second lateral edge; and
the pressure gradient decreases in pressure from the first longitudinal edge to the second longitudinal edge while remaining constant from the first lateral edge to the second lateral edge.

15. The variable pressure blanket of claim 14, wherein the pressure gradient is formed by a decrease in the density of the fill particles from the first longitudinal edge to the second longitudinal edge.

16. The variable pressure blanket of claim 14, wherein the pressure gradient is formed by a decrease in the quantity of fill particle from the first longitudinal edge to the second longitudinal edge.

17. A method of making the variable pressure blanket of claim 1, comprising:
depositing the fill particles onto a surface of the bottom fabric;
distributing the fill particles across the surface of the bottom fabric to the edges of the bottom fabric;
dividing the fill particles into the at least two discrete regions across the surface of the bottom fabric to form discrete regions, wherein one of the discrete regions includes more fill particles than the other of the discrete regions;
placing the top fabric over the bottom fabric;
aligning the edges of the top fabric with the edges of the bottom fabric; and
stitching the top fabric to the bottom fabric to form the casing and the pockets within each discrete region, wherein the pockets within a discrete region each have substantially the same density of fill particles.

18. The method of claim 17, further comprising:
depositing a first quantity of fill particles on the surface of the bottom fabric corresponding to one region of the at least two discrete regions; and
depositing a next quantity of fill particles on the surface of the bottom fabric corresponding to the other of the discrete regions;
wherein the first quantity of fill particles corresponds to a predetermined pressure and the next quantity of fill particles corresponds to a different predetermined pressure, such that the one discrete region generates a different pressure than the other discrete regions.

19. The method of claim 18, further comprising:
distributing the first quantity of fill particles across the one region of the at least two discrete regions; and
distributing the next quantity of fill particles across the other of the discrete regions;
wherein the first quantity is larger than the next quantity.

20. The method of claim 19, further comprising:
distributing the fill particles across the surface of the bottom fabric to all edges of the bottom fabric to evenly disperse the fill particles across the entire surface of the bottom fabric;
aligning the edges of the top fabric with the edges of the bottom fabric so that the top fabric and bottom fabric are coterminous when stitched; and
stitching a seam along the boundary of the at least two discrete regions to separate them via a seam.

\* \* \* \* \*